(12) United States Patent
Nakajima et al.

(10) Patent No.: US 9,650,351 B2
(45) Date of Patent: May 16, 2017

(54) INHIBITION OF IL-2 PRODUCTION

(71) Applicant: AYUMI PHARMACEUTICAL CORPORATION, Chuo-ku, Tokyo (JP)

(72) Inventors: Toshihiro Nakajima, Tokyo (JP); Satoko Aratani, Tokyo (JP); Kusuki Nishioka, Tokyo (JP); Hiroyuki Aono, Ikoma (JP)

(73) Assignee: AYUMI PHARMACEUTICAL CORPORATION, Tokyo (JP)

( * ) Notice: Subject to any disclaimer, the term of this patent is extended or adjusted under 35 U.S.C. 154(b) by 0 days.

(21) Appl. No.: 14/778,925

(22) PCT Filed: Mar. 19, 2014

(86) PCT No.: PCT/JP2014/057597
§ 371 (c)(1),
(2) Date: Sep. 21, 2015

(87) PCT Pub. No.: WO2014/148574
PCT Pub. Date: Sep. 25, 2014

(65) Prior Publication Data
US 2016/0046591 A1 Feb. 18, 2016

(30) Foreign Application Priority Data
Mar. 22, 2013 (JP) ................ 2013-060584

(51) Int. Cl.
*C07D 277/66* (2006.01)
*A61K 31/428* (2006.01)

(52) U.S. Cl.
CPC .......... *C07D 277/66* (2013.01); *A61K 31/428* (2013.01)

(58) Field of Classification Search
CPC .............. C07D 277/66; A61K 31/428
See application file for complete search history.

(56) References Cited

U.S. PATENT DOCUMENTS

| 4,479,949 A * | 10/1984 | Iwao | .................... C07D 277/66 514/233.8 |
| 7,642,274 B2 | 1/2010 | Shimomura et al. | |
| 2005/0113430 A1 | 5/2005 | Tokai et al. | |
| 2007/0117853 A1* | 5/2007 | Shimomura | ......... A61K 31/428 514/367 |
| 2010/0029575 A1 | 2/2010 | Junien et al. | |

FOREIGN PATENT DOCUMENTS

| JP | 2004-002352 A | 1/2004 |
| JP | 2005-041866 A | 2/2005 |
| JP | 2009-538316 A | 11/2009 |

OTHER PUBLICATIONS

Yamamoto et al., Journal of Medicinal Chemistry, (1988), 31(5), pp. 919-930.*

Chemical Abstracts Registry No. 1349578-95-5, indexed in the Registry file on STN CAS ONLINE Dec. 6, 2011.*
Rizos et al., Cytokine, 40, 2007, pp. 157-164.*
Greaves et al., The Lancet, Oct. 5, 1996, vol. 348, pp. 938-940.*
Doan et al., The Journal of Clinical Pharmacology, 2005, 45, pp. 751-762.*
International Search Report (PCT/ISA/210) mailed on May 27, 2014, by the Japanese Patent Office as the International Searching Authority for International Application No. PCT/JP2014/057597.
Written Opinion (PCT/ISA/237) mailed on May 27, 2014, by the Japanese Patent Office as the International Searching Authority for International Application No. PCT/JP2014/057597.
Y. Tsukahara-Ohsumi et al., "SA14867, a newly synthesized kappa-opioid receptor agonist with antinociceptive and antipruritic effects", European Journal of Pharmacology, 2010, pp. 62-67, vol. 647, No. 1-3.
Y. Tsukahara-Ohsumi et al., "The kappa opioid receptor agonist SA14867 has antinociceptive and weak sedative effects in models of acute and chronic pain", 2011, European Journal of Pharmacology, 2011, pp. 53-60, vol. 671, No. 1-3.
L. Guan et al., "Inhibition of T cell superantigen responses following treatment with the κ-opioid agonist U50,488H", Journal of Neuroimmunology, 1997, pp. 163-168, vol. 75.
L. Guan et al., "Modulation of DPK cell function by the kappa opioid agonist U50,488H", Advances in Experimental Medicine and Biology, 1998, pp. 125-136, vol. 437.
L. Guan et al., "Both T Cells and Macrophages Are Targets of κ-Opioid-Induced Immunosuppression", Brain, Behavior, and Immunity, 1994, pp. 229-240, vol. 8, No. 3.
P.K. Peterson et al., "κ-Opioid receptor agonist suppression of HIV-1 expression in CD4+lymphocytes", Biochemical Pharmacology, 2001, pp. 1145-1151, vol. 61.
Y. Okamoto et al., "Cytokine Balance in the Pathogenesis of Rheumatoid Arthritis", Yakugaku Zasshi, 2001, pp. 131-138, vol. 121, No. 2.

(Continued)

*Primary Examiner* — Laura L Stockton
(74) *Attorney, Agent, or Firm* — Buchanan, Ingersoll & Rooney PC

(57) ABSTRACT

An object is to find a substance which inhibits IL-2 production.

IL-2 production can be inhibited by a compound represented by the following formula (I):

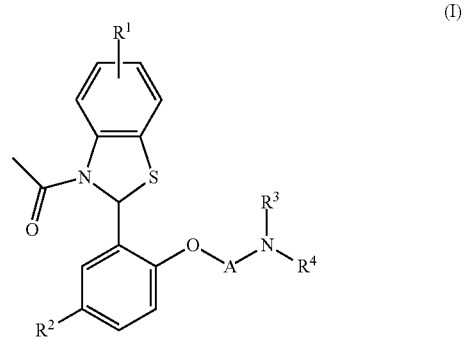

wherein $R^1$ to $R^4$ and A are as defined in the present specification,
or a pharmaceutically acceptable salt thereof.

5 Claims, No Drawings

(56) References Cited

OTHER PUBLICATIONS

Ackali et al., *Serum concentrations of interleukin-2 and tumour necrosis factor-α under cyclosporine versus acitretin treatment in plaque-type psoriasis*, 42(5) Journal of International Medical Research 1118-1122 (2014).
Jegasothy et al., *Tacrolimus (FK 506)—A New Therapeutic Agent for Severe Recalcitrant Psoriasis*, 128(6) Arch Dermatol. 781-785 (1992).
Dam et al., *1α,25-Dihydroxycholecalciferol and Cyclosporine Suppress Induction and promote Resolution of Psoriasis in Human Skin Grafts Transplanted on to SCID Mice*, 113(6) The Journal of Investigative Dermatology 1082-1089 (Dec. 6, 1999).
Filaci et al., *Long-term treatment of patients affected by systemic sclerosis with cyclosporine A*, 40 Rheumatology 1431-1432 (2001).
Géher et al., *Repeated cyclosporine therapy of peripheral arthritis associated with ankylosing spondylitis*, 7(1) Med. Sci. Monit 105-107 (2001).
Landewéet al., *Chloroquine inhibits T cell proliferation by interfering with IL-2 production and responsiveness*, 102 Clin. Exp. Immunol. 144-151 (1995).
Morton et al., *Cyclosporin and tacrolimus: their use in a routine clinical setting for scleroderma*, 39 Rheumatology 865-869 (2000).
Obayashi et al., *Dosing Time-Dependency of the Arthritis-Inhibiting Effect of Tacrolimus in Mice*, 116 J. Pharmacol Sci 264-273 (2011).
Shiratsuchi et al., *Successful treatment of pure red cell aplasia and autoimmune cytopenia with cyclosporine and prednisolone in a patient with Sjögren's syndrome*, 13 Modern Rheumatology 363-366 (2003).
Song et al. *Reversing Interleukin-2 Inhibition Mediated by Anti-Double-Stranded DNA Autoantibody ameliorates Glomerulonephritis in MRL*-Ipr/Ipr *Mice* 62(8) Arthritis & Rheumatism 2401-2411 (Aug. 2010).
Tanaka et al., *Treatment of young patients with lupus nephritis using calcineurin inhibitors*, 1(6) World Journal of Nephrology, 177-183 (Dec. 6, 2012).

\* cited by examiner

INHIBITION OF IL-2 PRODUCTION

TECHNICAL FIELD

The present invention relates to an IL-2 production inhibitor or a prophylactic or therapeutic agent of IL-2 related diseases.

BACKGROUND ART

IL-2 (Interleukin-2) is a kind of cytokines, is produced mainly by activated T cells, and acts on the cells such as T cells, B cells, macrophages, etc. The IL-2 shows proliferation and activation of T cells, proliferation and acceleration of antibody-producing ability of B cells, activation of monocytes and macrophages, proliferation and activation of natural killer cells (NK cell), and inducing action of lymphokine-activated killer cells, etc. On the cell membrane of T cells, T cell antigen receptor (T Cell Receptor, TCR) is expressed, and T cells produce IL-2 by receiving antigen presentation from antigen presenting cells such as macrophages, etc.

It has been known that TCR existing on the surface of the T cell is being present by forming a complex with a molecule which is the so-called CD4. When an antigen is bound to TCR, phosphorylation of TCR is carried out by kinase in the cell. Phospholipase C (PLC) γ participates in release of calcium ion from endoplasmic reticulum, and activations of calmodulin and calcineurin are calcium-dependently induced. Calcineurin is to carry out dephosphorylation of a transcription factor NF-AT to transfer into a nucleus. Thereafter, NF-AT is bound to an IL-2 promotor, and production of IL-2 mRNA is accelerated.

Tacrolimus (FK506) and cyclosporine A which are immunosuppressants inhibit IL-2 production at the T cells. These drugs bind to cyclophilin and FK506-binding protein (FKBP) in the cells, and the complexes of the drug-protein bind to calcineurin. As stated above, calcineurin is an important molecule in transcriptional control of IL-2, and according to this mechanism, dephosphorylation of the calcineurin-dependent transcription factor NF-AT is inhibited, and as a result, an immunosuppressing action is expressed. These drugs have been mainly used for the purpose of suppressing rejection after organ transplantation. In addition, tacrolimus, etc., have also been used for the treatment of atopic dermatitis.

It has been reported that cytokines such as IL-2, etc., are deeply participated in bronchial asthma, etc. (Non-Patent Documents 1 to 2).

Further, it has been known that cytokine balance is participated in onset of rheumatoid arthritis, in particular, Th1 type cytokine such as IL-2, etc., plays a role of promoting onset of arthritis (Non-Patent Document 3).

In addition, production of IL-2 has been known to participate in the diseases such as AIDS, cancer, skin diseases (psoriasis, atopic dermatitis, urticaria), internal diseases (lupus nephritis), ophthalmic diseases (allergic conjunctivitis, sty, chalazion, spring catarrh, uveitis, cancer), autoimmune diseases (polymyositis, Hashimoto's disease, Behcet's disease, ankylosing spondylitis, systemic sclerosis, Sjogren's syndrome, pollenosis, scleroderma), gastrointestinal diseases, inflammatory diseases (gout, psoriatic arthritis, rheumatoid arthritis), central nervous system diseases (multiple sclerosis), respiratory diseases (asthma, chronic obstructive pulmonary disease), fibromyalgia, myasthenia gravis, sarcoidosis, nasal inflammation, nasal catarrh, etc.

On the other hand, in JP Patent No. 4,296,345 (Patent Document 1), JP Patent No. 5061134 (Patent Document 2) and JP Patent No. 4360292 (Patent Document 3), it has been shown that some of 2-phenylbenzothiazoline derivatives have been specifically disclosed, and these act as a κ opioid receptor agonist, and are useful as a therapeutic agent and pain threshold decrease inhibitor of pain, pruritus, etc.

Also, (+)-3-acetyl-6-chloro-2-[2-(3-(N-(2-ethoxyethyl)-N-isopropylamino)propoxy)-5-methoxyphenyl]benzothiazoline (−)-O,O'-diacetyl-L-tartarate which is one of the 2-phenylbenzothiazoline derivatives has been disclosed in European Journal of Pharmacology (2010), 647 (1-3), 62-67 (Non-Patent Document 4) and European Journal of Pharmacology (2011), 671 (1-3), 53-60 (Non-Patent Document 5), and shown that it has an antinociceptive action, an antipruritic action and a weak sedative action.

However, a relation between these 2-phenylbenzothiazoline derivatives and production of IL-2 has never been reported as of today, and it has never been known that the 2-phenylbenzothiazoline derivatives have an inhibiting action of IL-2 production as a matter of course.

FK506 and cyclosporine, and a steroidal anti-inflammatory drug also have an inhibiting action of IL-2 production. These medicaments have been used for various treatments, however, there are problems that potent side effects appears by administration for a long period of time, etc., and a safe medicament having high safety and effectiveness has not yet been found out. Therefore, it has been desired to develop a drug having a potent IL-2 production inhibiting action and safety.

PRIOR ART DOCUMENTS

Patent Documents

Patent Document 1: JP Patent No. 4,296,345
Patent Document 2: JP Patent No. 5,061,134
Patent Document 3: JP Patent No. 4,360,292

Non-Patent Document

Non-Patent Document 1: Proc. Natl. Acad. Sci. USA 85:2288-92, 1988
Non-Patent Document 2: Akutsu, I. et al., Antibody against interleukin-5 prevents antigen-induced eosinophil infiltration and bronchial hyperreactivity in the guinea pig airways. Immunol. Lett. 1995, 45, 109
Non-Patent Document 3: Yoshihiro Okamoto et al., "Onset of rheumatoid arthritis and cytokine balance", Yakugaku Zasshi, 121 (2), 131-138 (2001)
Non-Patent Document 4: European Journal of Pharmacology (2010), 647 (1-3), 62-67
Non-Patent Document 5: European Journal of Pharmacology (2011), 671 (1-3), 53-60

SUMMARY OF THE INVENTION

Problems to be Solved by the Invention

An object is to find out a compound which inhibits IL-2 production, and to provide an IL-2 production inhibitor containing the compound as an active ingredient or a prophylactic or therapeutic agent of IL-2 related diseases.

Means for Solving the Problems

The present inventors have intensively studied to find out a substance which inhibits IL-2 production, and as a result, they have found out a compound represented by the formula (I):

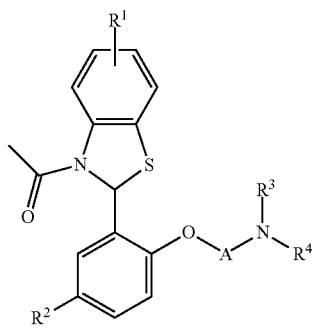

wherein

A represents a lower alkylene group;

R¹ represents a hydrogen atom, a halogen atom, a lower alkyl group or a lower alkyl group substituted by a halogen atom;

R² represents a hydrogen atom, a halogen atom, a lower alkyl group or a lower alkoxy group;

R³ and R⁴ each may be the same or different from each other and represent a hydrogen atom, a lower alkyl group, a lower alkyl group substituted by a hydroxyl group, a lower alkyl group substituted by a lower alkoxy group, a lower alkyl group substituted by a lower alkoxy group which is substituted by a lower alkoxy group or a lower alkyl group substituted by an acetoxy group, or a pharmaceutically acceptable salt thereof (in the following, these are also collectively called as "the present compound") can inhibit IL-2 production, and found out an IL-2 production inhibitor or a prophylactic or therapeutic agent of IL-2 related diseases, which contains the present compound as an active ingredient, and whereby they have accomplished the present invention.

That is, the present invention relates to the following.

(1) An IL-2 production inhibitor which comprises a compound represented by the formula (I):

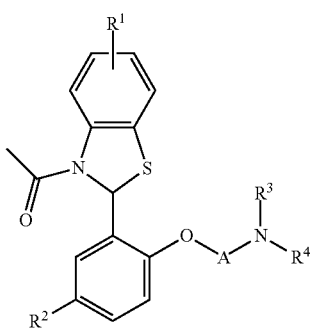

wherein

A represents a lower alkylene group;

R¹ represents a hydrogen atom, a halogen atom, a lower alkyl group or a lower alkyl group substituted by a halogen atom;

R² represents a hydrogen atom, a halogen atom, a lower alkyl group or a lower alkoxy group; and R³ and R⁴ each may be the same or different from each other and represent a hydrogen atom, a lower alkyl group, a lower alkyl group substituted by a hydroxyl group, a lower alkyl group substituted by a lower alkoxy group, a lower alkyl group substituted by a lower alkoxy group which is substituted by a lower alkoxy group or a lower alkyl group substituted by an acetoxy group, or a pharmaceutically acceptable salt thereof as an active ingredient.

(2) The IL-2 production inhibitor described in the above-mentioned (1), wherein the compound represented by the formula (I) is a compound where A represents a lower alkylene group;

R¹ represents a halogen atom;

R² represents a lower alkoxy group;

R³ represents a lower alkyl group; and

R⁴ represents a lower alkyl group substituted by a hydroxyl group, a lower alkyl group substituted by a lower alkoxy group, a lower alkyl group substituted by a lower alkoxy group which is substituted by a lower alkoxy group or a lower alkyl group substituted by an acetoxy group.

(3) The IL-2 production inhibitor described in the above-mentioned (1) or (2), wherein the compound represented by the formula (I) is a compound where A represents trimethylene group or a 1-methyltrimethylene group;

R¹ represents chlorine atom;

R² represents methoxy group;

R³ represents isopropyl group; and

R⁴ represents 2-hydroxyethyl group, 2-methoxyethyl group, 2-ethoxyethyl group, 2-(methoxymethoxy)ethyl group or 2-acetoxyethyl group.

(4) The IL-2 production inhibitor described in the above-mentioned any one of (1) to (3), wherein the compound represented by the formula (I) is (+)-3-acetyl-6-chloro-2-[2-(3-(N-(2-ethoxyethyl)-N-isopropylamino)propoxy)-5-methoxyphenyl]benzothiazoline, (±)-3-acetyl-6-chloro-2-[2-(3-(N-(2-ethoxyethyl)-N-isopropylamino)propoxy)-5-methoxyphenyl]benzothiazoline, (+)-3-acetyl-6-chloro-2-[2-(3-(N-(2-hydroxyethyl)-N-isopropylamino)propoxy)-5-methoxyphenyl]benzothiazoline or (+)-3-acetyl-6-chloro-2-[2-(3-(N-isopropyl-N-(2-methoxyethyl)amino)propoxy)-5-methoxyphenyl]benzothiazoline.

(5) The IL-2 production inhibitor described in the above-mentioned any one of (1) to (4), wherein a pharmaceutically acceptable salt of the compound represented by the formula (I) is a (−)-O,O'-diacetyl-L-tartaric acid salt or a hydrochloric acid salt.

(6) The IL-2 production inhibitor described in the above-mentioned any one of (1) to (5), wherein the IL-2 production inhibitor is a prophylactic or therapeutic agent of IL-2 related diseases.

Further, the present invention relates to the following.

(7) The above-mentioned compound represented by the formula (I) or a pharmaceutically acceptable salt thereof for the use of prophylaxis or treatment of IL-2 related diseases.

(8) Use of the above-mentioned compound represented by the formula (I) or a pharmaceutically acceptable salt thereof for the manufacture of a medicine for prophylaxis or treatment of IL-2 related diseases.

(9) A pharmaceutical composition for prophylaxis or treatment of IL-2 related diseases which comprises a therapeutically effective amount of the above-mentioned compound represented by the formula (I) or a pharmaceutically acceptable salt thereof and an excipient.

(10) A method for prophylaxis or treatment of IL-2 related diseases which comprises administering an effective amount of the above-mentioned compound represented by the formula (I) or a pharmaceutically acceptable salt thereof.

(11) The above-mentioned compound represented by the formula (I) or a pharmaceutically acceptable salt thereof for the use of inhibition of IL-2 production.

(12) A composition for inhibiting IL-2 production which comprises the above-mentioned compound represented by the formula (I) or a pharmaceutically acceptable salt thereof.

(13) Use of the above-mentioned compound represented by the formula (I) or a pharmaceutically acceptable salt thereof for inhibiting IL-2 production.

(14) Use of the above-mentioned compound represented by the formula (I) or a pharmaceutically acceptable salt thereof for the manufacture of a composition for inhibiting IL-2 production.

(15) A method for inhibiting IL-2 production which comprises administering the above-mentioned compound represented by the formula (I) or a pharmaceutically acceptable salt thereof.

Effect of the Invention

It can be provided an IL-2 production inhibitor or a prophylactic or therapeutic agent of IL-2 related diseases which contains the present compound of the present invention as an active ingredient.

BEST MODE TO CARRY OUT THE INVENTION

In the following, definitions of the terms (an atom, a group, etc.) used in the claims and the specification are explained in detail.

"The halogen atom" represents fluorine, chlorine, bromine or iodine atom.

"The lower alkyl group" represents a linear or branched alkyl group having 1 to 8 carbon atoms, preferably a linear or branched alkyl group having 1 to 6 carbon atoms. Specific examples may include methyl group, ethyl group, n-propyl group, n-butyl group, n-pentyl group, n-hexyl group, n-heptyl group, n-octyl group, isopropyl group, isobutyl group, sec-butyl group, tert-butyl group, isopentyl group, etc.

"The lower alkoxy group" mean a group in which a hydrogen atom of the hydroxyl group is substituted by the above-mentioned lower alkyl group. Specific examples may include methoxy group, ethoxy group, n-propoxy group, n-butoxy group, n-pentoxy group, n-hexyloxy group, n-heptyloxy group, n-octyloxy group, isopropoxy group, isobutoxy group, sec-butoxy group, tert-butoxy group, isopentyloxy group, etc.

"The lower alkylene group" mean a linear or branched lower alkylene group having 1 to 8 carbon atoms, preferably a linear or branched lower alkylene group having 1 to 6 carbon atoms. Specific examples may include methylene group, ethylene group, trimethylene group, tetramethylene group, pentamethylene group, hexamethylene group, heptamethylene group, octamethylene group, methylmethylene group, ethylmethylene group, 1-methylethylene group, 1-methyltrimethylene, etc.

"The lower alkyl group substituted by a halogen atom" mean the above-mentioned lower alkyl group substituted by one or a plural number of halogen atoms. Specific examples may include trifluoromethyl group, trichloromethyl group, etc.

"The lower alkyl group substituted by a hydroxyl group" mean the above-mentioned lower alkyl group substituted by one or a plural number of hydroxyl groups. Specific examples may include 2-hydroxyethyl group, 3-hydroxypropyl group, etc.

"The lower alkyl group substituted by a lower alkoxy group" mean the above-mentioned lower alkyl group substituted by one or a plural number of lower alkoxy groups. Specific examples may include 2-methoxyethyl group, 2-ethoxyethyl group, 3-methoxypropyl group, 3-ethoxypropyl group, etc.

"The lower alkyl group substituted by a lower alkoxy group which is substituted by a lower alkoxy group" mean the above-mentioned lower alkyl group having one lower alkoxy group substituted by one lower alkoxy group as a substituent. Specific examples may include 2-(methoxymethoxy)ethyl group, 3-(methoxy-methoxy)propyl group, etc.

"The lower alkyl group substituted by an acetoxy group" mean the above-mentioned lower alkyl group substituted by one or a plural number of acetoxy groups. Specific examples may include 2-acetoxyethyl group, 3-acetoxypropyl group, etc.

"The plural number of substituents" mean the substituents of 2 or more and less than the number capable of substituting at the portion to be substituted. The respective substituents may be the same or different from each other, and the number of the substituents is preferably 2 or 3.

Also, in the present invention, a hydrogen atom or a halogen atom is also included in the concept of "the substituent".

The pharmaceutically acceptable salt in the present invention is not particularly limited so long as it is a pharmaceutically acceptable salt, and may include a salt with an inorganic acid, a salt with an organic acid, a quaternary ammonium salt, a salt with a halogen ion, etc. The salt with an inorganic acid may include a salt with hydrochloric acid, hydrobromic acid, hydroiodic acid, nitric acid, sulfuric acid, phosphoric acid, etc. The salt with an organic acid may include a salt with acetic acid, oxalic acid, fumaric acid, maleic acid, succinic acid, citric acid, tartaric acid, diacetyl tartaric acid, adipic acid, gluconic acid, glucoheptonic acid, glucuronic acid, terephthalic acid, methanesulfonic acid, lactic acid, hippuric acid, 1,2-ethanedisulfonic acid, isethionic acid, lactobionic acid, oleic acid, pamoic acid, polygalacturonic acid, stearic acid, tannic acid, trifluoromethanesulfonic acid, benzenesulfonic acid, p-toluenesulfonic acid, lauryl sulfate, methyl sulfate, naphthalenesulfonic acid, sulfosalicylic acid, etc. The quaternary ammonium salt may include a salt with methyl bromide, methyl iodide, etc. The salt with a halogen ion may include a salt with chloride ion, bromide ion, iodide ion, etc. The pharmaceutically acceptable salt in the present invention is preferably hydrochloride and O,O'-diacetyltartaric acid salt, particularly preferably (−)-O,O'-diacetyl-L-tartaric acid salt.

The present compound in the present invention may be in the form of a hydrate or a solvate.

When geometric isomers, tautomeric isomers, optical isomers, enantiomers or diastereoisomers are present in the present compound of the present invention, these isomers are included in the scope of the present invention.

Further, when crystal polymorphism is present in the present compound, the crystal polymorph is included in the scope of the present invention.

(a) As preferred examples in the present compound, they may include a compound or a pharmaceutically acceptable salt thereof, in the compound represented by the formula (I), wherein each group is a group mentioned below.

(a1) A represents a lower alkylene group; and/or
(a2) $R^1$ represents a halogen atom; and/or
(a3) $R^2$ represents a lower alkoxy group; and/or
(a4) $R^3$ represents a lower alkyl group; and/or
(a5) $R^4$ represents a lower alkyl group substituted by a hydroxyl group, a lower alkyl group substituted by a lower alkoxy group, a lower alkyl group substituted by a lower alkoxy group which is substituted by a lower alkoxy group or a lower alkyl group substituted by an acetoxy group.

That is, in the compound represented by the formula (I), a compound comprising one or two or more of each combination selected from the above-mentioned (a1), (a2), (a3), (a4) and (a5) or a pharmaceutically acceptable salt thereof may be included as a preferred example. In the compound represented by the formula (I), a compound comprising all the combinations of the above-mentioned (a1), (a2), (a3), (a4) and (a5) or a pharmaceutically acceptable salt thereof may be included as a particularly preferred example.

(b) Preferred examples in the present compound may include, in the compound represented by the formula (I), a compound of which the respective groups are the groups shown below or a pharmaceutically acceptable salt thereof.

(b1) A represents trimethylene group or 1-methyltrimethylene group; and/or
(b2) $R^1$ represents chlorine atom; and/or
(b3) $R^2$ represents methoxy group; and/or
(b4) $R^3$ represents isopropyl group; and/or
(b5) $R^4$ represents 2-hydroxyethyl group, 2-methoxy ethyl group, 2-ethoxy ethyl group, 2-(methoxymethoxy) ethyl group or 2-acetoxyethyl group.

That is, in the compound represented by the formula (I), a compound comprising one or two or more of each combination selected from the above-mentioned (b1), (b2), (b3), (b4) and (b5) or a pharmaceutically acceptable salt thereof may be included as a preferred example. Also, the selected conditions may be combined with the conditions of (a). In the compound represented by the formula (I), a compound comprising all the combinations of the above-mentioned (b1), (b2), (b3), (b4) and (b5) or a pharmaceutically acceptable salt thereof may be included as a particularly preferred example.

(c) Preferred examples in the present compound may include,
3-acetyl-6-chloro-2-[2-(3-(N-(2-hydroxyethyl)-N-isopropylamino)propoxy)-5-methoxyphenyl]benzothiazoline,
3-acetyl-6-chloro-2-[2-(3-(N-isopropyl-N-(2-methoxyethyl)amino)propoxy)-5-methoxyphenyl]benzothiazoline,
3-acetyl-6-chloro-2-[2-(3-(N-(2-ethoxyethyl)-N-isopropylamino)propoxy)-5-methoxyphenyl]benzothiazoline,
3-acetyl-6-chloro-2-[2-(3-(N-isopropyl-N-(2-(methoxymethoxy)ethyl)amino)-propoxy)-5-methoxyphenyl]benzothiazoline,
2-[2-(3-(N-(2-acetoxyethyl)-N-isopropylamino)propoxy)-5-methoxyphenyl]-3-acetyl-6-chlorobenzothiazoline,
3-acetyl-6-chloro-2-[2-(3-(N-(2-hydroxyethyl)-N-isopropylamino)-1-methyl-propoxy)-5-methoxyphenyl]benzothiazoline,
3-acetyl-6-chloro-2-[2-(3-(N-isopropyl-N-(2-methoxyethyl)amino)-1-methyl-propoxy)-5-methoxyphenyl]benzothiazoline,
3-acetyl-6-chloro-2-[2-(3-(N-(2-ethoxyethyl)-N-isopropylamino)-1-methyl-propoxy)-5-methoxyphenyl]benzothiazoline,
3-acetyl-6-chloro-2-[2-(3-(N-isopropyl-N-(2-(methoxymethoxy)ethyl)amino)-1-methylpropoxy)-5-methoxyphenyl]benzothiazoline,
2-[2-(3-(N-(2-acetoxyethyl)-N-isopropylamino)-1-methyl-propoxy)-5-methoxy-phenyl]-3-acetyl-6-chlorobenzothiazoline, or a pharmaceutically acceptable salt thereof.

(d) The most preferred examples in the present compound may include, (+)-3-acetyl-6-chloro-2-[2-(3-(N-(2-ethoxyethyl)-N-isopropylamino)propoxy)-5-methoxyphenyl]benzothiazoline represented by the formula (II):

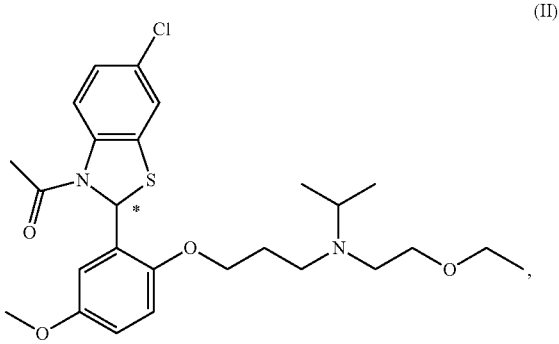 [SMILES: CCOCCN(CCCOc1ccc(OC)cc1C1Sc2cc(Cl)ccc2N1C(C)=O)C(C)C]

(+)-3-acetyl-6-chloro-2-[2-(3-(N-(2-ethoxyethyl)-N-isopropylamino)propoxy)-5-methoxyphenyl]benzothiazoline (−)-O,O'-diacetyl-L-tartaric acid salt represented by the formula (III):

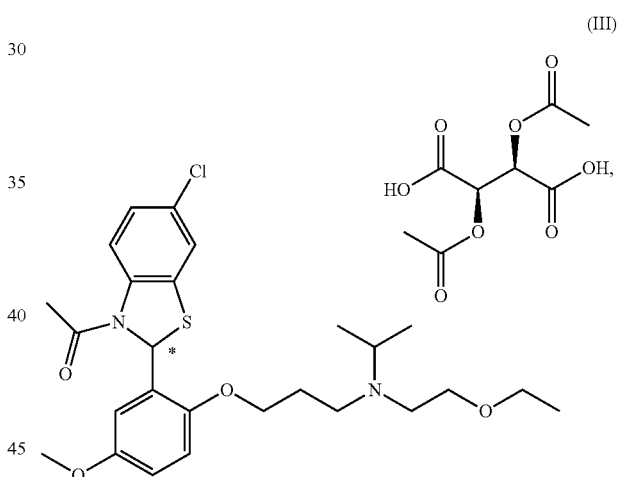

(±)-3-acetyl-6-chloro-2-[2-(3-(N-(2-ethoxyethyl)-N-isopropylamino)propoxy)-5-methoxyphenyl]benzothiazoline hydrochloride represented by the formula (IV):

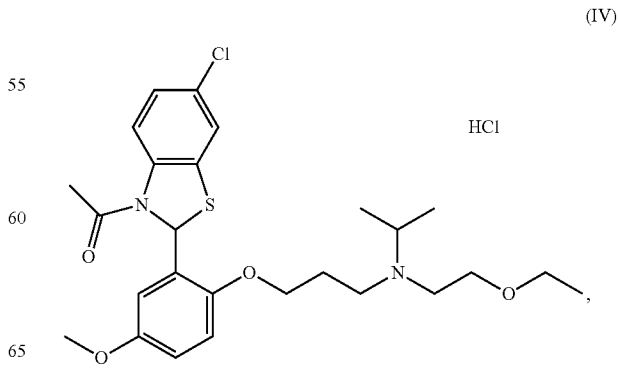

(+)-3-acetyl-6-chloro-2-[2-(3-(N-(2-hydroxyethyl)-N-isopropylamino)propoxy)-5-methoxyphenyl]benzothiazoline hydrochloride represented by the formula (V):

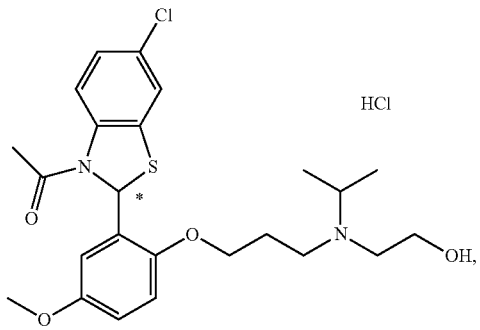

and (+)-3-acetyl-6-chloro-2-[2-(3-(N-isopropyl-N-(2-methoxyethylamino)propoxy)-5-methoxyphenyl]benzothiazoline (−)-O,O'-diacetyl-L-tartaric acid salt represented by the formula (VI):

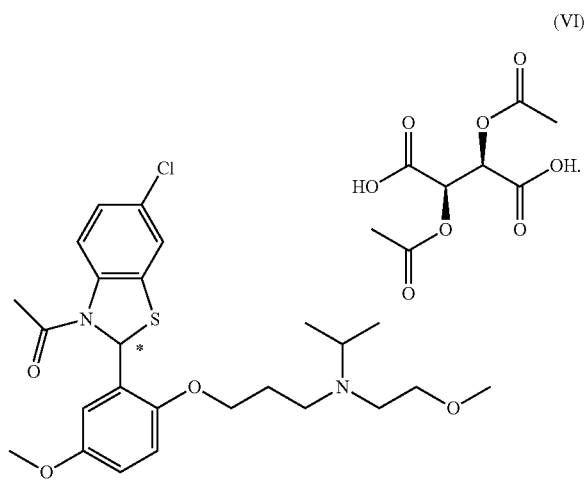

The compounds represented by the above-mentioned formulae (II), (III), (V) and (VI) have an asymmetric carbon at the 2-position of the benzothiazoline ring, but the absolute configuration thereof is unknown.

The present compound in the present invention can be prepared, isolated and purified by the conventional manner in the field of the organic synthetic chemistry, and may be synthesized by the methods disclosed in, for example, JP Patent No. 4,296,345 or JP Patent No. 5,061,134. In addition with regard to geometric isomers, tautomeric isomers, optical isomers, enantiomers or diastereoisomers of the present compound in the present invention, these isomers can be prepared, isolated and purified by the conventional manner, for example, column chromatography or HPLC, etc.

The IL-2 production inhibitor in the present invention means an inhibitor which mainly inhibits production of IL-2 by activated T cells. The IL-2 production inhibitor can be used for prophylaxis or treatment of various kinds of disease group caused by excess activation of T cells or proliferation of T cells, by inhibiting IL-2 production.

The IL-2 related diseases in the present invention are diseases caused by IL-2 production or acceleration of IL-2 receptor expression, etc., which have been known as a common sense in this field of the art. IL-2 related diseases may include, for example, AIDS, cancer, skin diseases (psoriasis, atopic dermatitis, urticaria), internal diseases (lupus nephritis), ophthalmic diseases (allergic conjunctivitis, sty, chalazion, spring catarrh, uveitis, cancer), autoimmune diseases (polymyositis, Hashimoto's disease, Behcet's disease, ankylosing spondylitis, systemic sclerosis, Sjogren's syndrome, pollenosis, scleroderma), gastrointestinal diseases, inflammatory diseases (gout, psoriatic arthritis, rheumatoid arthritis), central nervous system diseases (multiple sclerosis), respiratory diseases (asthma, chronic obstructive pulmonary disease), fibromyalgia, myasthenia gravis, sarcoidosis, nasal inflammation and nasal catarrh.

The IL-2 production inhibitor or a prophylactic or therapeutic agent of IL-2 related diseases of the present invention may be administered orally or parenterally, and no particular technique is required for formulating these agents, and these can be formulated by using generally employed technique. The dosage form may include tablets, capsules, granules, powders, injections, eye drops, ointments, etc.

When these are made an oral agent such as tablets, capsules, granules, powders, etc., an excipient, a lubricant, a binder, a disintegrator, a coating agent, a film-forming agent, a stabilizer, a corrigent, etc., may be added depending on necessity and the oral agent can be prepared. The excipient may include lactose, mannitol, crystalline cellulose, starch, vegetable oil, light anhydrous silicic acid, calcium carbonate, calcium hydrogen phosphate, etc., the lubricant may include stearic acid, magnesium stearate, talc, etc., the binder may include starch, hydroxypropyl cellulose, hydroxypropylmethyl cellulose, polyvinylpyrrolidone, etc., the disintegrator may include carboxymethyl cellulose, carboxymethyl cellulose calcium, a low substituted hydroxypropyl cellulose, a low substituted hydroxypropylmethyl cellulose, calcium citrate, etc., the coating agent may include hydroxypropylmethyl cellulose, macrogol, a silicone resin, etc., the film-forming agent may include a gelatin coating film, etc., the stabilizer may include ethyl paraoxybenzoate, benzyl alcohol, etc., and the corrigent may include a sweetener, an acidifier, a flavoring agent, etc.

When these are made a parenteral agent such as injections, eye drops, etc., an isotonicifier, a buffering agent, a surfactant, a stabilizer, an anticeptic, etc., may be added depending on necessity and the parenteral agent can be prepared. The isotonicifier may include sodium chloride, concentrated glycerin, etc., the buffering agent may include sodium phosphate, sodium acetate, boric acid, borax, citric acid, etc., the surfactant may include polyoxyethylene sorbitan monooleate, polyoxyl stearate, polyoxyethylene hardened castor oil, etc., a stabilizer may include sodium citrate, sodium edetate, etc., and as the anticeptic, an anticeptic such as benzalkonium chloride, paraben, etc., may include.

A pH of the eye drops may be within the range acceptable for an ophthalmic preparation, and it is preferably in the range of pH 4 to 8, more preferably in the range of pH 5 to 7.

When these are made an ointment, it can be prepared by using a generally employed base, and the base may include white petrolatum, liquid paraffin, etc.

An administration dose of the present compound and a pharmaceutically acceptable salt thereof may be optionally changed depending on a dosage form, severity of the symptoms, an age, a body weight or an administration route of a subject to be administered (a human or an animal, etc.), and a judgment of a doctor, etc.

In the case of the oral agent, it can be generally administered, for example, an administration dose per a day within the range of 0.1 to 5,000 mg, preferably 1 to 1,000 mg once or divided into several times.

In the case of the eye drops or the intercalating agent, it can be generally administered, for example, an administration dose per a day within the range of 0.01 to 500 µg, preferably within the range of 0.05 to 100 µg once a day or divided into several times. The concentration of the present compound in the eye drops is not particularly limited, and eye drops can be dropped to eyes at a concentration within the range of 0.00001 to 3 w/v %, preferably within the range of 0.0001 to 1 w/v %. The concentration of the eye drops may be any value calculated based on the weight of either a free form of the present compound and a salt thereof.

In the case of the ointments, it can be generally administered, for example, an administration dose per a day within the range of 0.0001 to 50 mg, preferably within the range of 0.0003 to 20 mg once or divided into several times.

The IL-2 production inhibitor and the prophylactic or therapeutic agent of a IL-2 related diseases of the present invention may be used in combination with a nonsteroidal anti-inflammatory agent such as indomethacin, ibuprofen, diclofenac, aspirin, etc.; a steroidal anti-inflammatory agent such as dexamethasone, betamethasone, prednisolone, triamcinolone, etc.; an immunosuppressant such as tacrolimus, cyclosporine, sirolimus, etc.; an antihistamine such as diphenhydramine, chlorpheniramine, triprolidine, promethazine, alimemazine, hydroxyzine, cyproheptadine, fexofenadine, olopatadine, epinastine, loratadine, cetirizine, bepotastine, mequitazine, etc.; an antirheumatic drug such as bucillamine, salazosulfapyridine, methotrexate, etc.; and a biological preparation such as infliximab, adalimumab, tocilizumab, etc.

EXAMPLES

In the following, synthetic examples, preparation examples and pharmacological tests of the present compound are shown, but these are intended for better understanding of the present invention, and are not intended to limit the scope of the present invention.

SYNTHETIC EXAMPLES OF THE PRESENT COMPOUNDS

Synthetic Example 1

Synthesis of (+)-3-acetyl-6-chloro-2-[2-(3-(N-(2-ethoxyethyl)-N-isopropyl-amino)propoxy)-5-methoxyphenyl]benzothiazoline (Compound 1)

To an anhydrous N,N-dimethylformamide (25 mL) solution containing (+)-3-acetyl-6-chloro-2-[2-(3-chloropropoxy)-5-methoxyphenyl]benzothiazoline (Reference compound 14-1 described in JP Patent No. 5,061,134, 5.0 g, 12 mmol) were added an anhydrous N,N-dimethylformamide (10 mL) solution containing N-(2-ethoxyethyl)isopropylamine (Reference compound 20-1 described in JP Patent No. 5,061,134, 2.4 g, 18 mmol), potassium carbonate (3.4 g, 25 mmol) and sodium iodide (3.7 g, 25 mmol), and the resulting mixture was stirred at 60° C. overnight. To the reaction mixture was added water (200 mL), and the mixture was extracted with ethyl acetate (120 mL). The organic layer was washed with water (200 mL), a saturated aqueous ammonium chloride solution (200 mL) and a saturated saline solution (200 mL), and dried over anhydrous sodium sulfate. After the solvent was distilled off under reduced pressure, the residue was purified by silica gel column chromatography to obtain 4.6 g of the title compound. (Yield: 75%)

$^1$H-NMR (400 MHz, CDCl$_3$) δ1.02 (d, J=6.6 Hz, 6H), 1.17-1.21 (m, 3H), 1.90-1.97 (m, 2H), 2.14 (brs, 3H), 2.60-2.74 (m, 4H), 2.93-3.00 (m, 1H), 3.44-3.51 (m, 4H), 3.66 (s, 3H), 4.04-4.13 (m, 2H), 6.58-6.60 (m, 1H), 6.75-6.85 (m, 3H), 7.00-7.04 (m, 1H), 7.08 (dd, J=2.2, 8.5 Hz, 1H), 8.16 (brs, 1H)

$[\alpha]_D^{20}$+513.0 (c=1.00, methanol)

Synthetic Example 2

Synthesis of (+)-3-acetyl-6-chloro-2-[2-(3-(N-(2-ethoxyethyl)-N-isopropyl-amino)propoxy)-5-methoxyphenyl]benzothiazoline (-)-O,O'-diacetyl-L-tartaric acid salt (Compound 2)

To (+)-3-acetyl-6-chloro-2-[2-(3-(N-(2-ethoxyethyl)-N-isopropylamino)-propoxy)-5-methoxyphenyl]benzothiazoline (Compound 1, 7.69 g, 15.2 mmol) were added (-)-O,O'-diacetyl-L-tartaric acid (3.56 g, 15.2 mmol) and 47.5 mL of ethyl acetate, and the mixture was stirred at room temperature for one hour. The residue obtained by distilling the solvent under reduced pressure was solidified by using ethyl acetate and methyl tert-butyl ether to obtain 8.95 g of the title compound. (Yield: 79%)

$^1$H-NMR (500 MHz, DMSO-d$_6$, 70° C.) 1.08-1.10 (m, 9H), 1.93-2.00 (m, 2H), 2.05 (s, 6H), 2.18 (brs, 3H), 2.85-2.95 (m, 4H), 3.20-3.28 (m, 1H), 3.46 (q, J=7.2 Hz, 2H), 3.50-3.54 (m, 2H), 3.60 (s, 3H), 4.05-4.15 (m, 2H), 5.37 (s, 2H), 6.49 (d, J=3.1 Hz, 1H), 6.87 (dd, J=3.1, 8.8 Hz, 1H), 6.97-7.05 (m, 2H), 7.18 (dd, J=2.4, 8.8 Hz, 1H), 7.31 (d, J=2.4 Hz, 1H), 7.97 (brs, 1H)

$[\alpha]_D^{20}$+314.2 (c=1.00, methanol)

According to Synthetic Examples 1 and 2, and the method described in JP Patent No. 4,296,345 or JP Patent No. 5,061,134, (±)-3-acetyl-6-chloro-2-[2-(3-(N-(2-ethoxyethyl)-N-isopropylamino)propoxy)-5-methoxyphenyl]benzothiazoline hydrochloride (Compound 3), (+)-3-acetyl-6-chloro-2-[2-(3-(N-(2-hydroxyethyl)-N-isopropylamino)propoxy)-5-methoxyphenyl]benzothiazoline hydrochloride (Compound 4) and (+)-3-acetyl-6-chloro-2-[2-(3-(N-isopropyl-N-(2-methoxyethyl)amino)propoxy)-5-methoxyphenyl]benzothiazoline (-)-O,O'-diacetyl-L-tartaric acid salt (Compound 5) were synthesized.

PREPARATION EXAMPLE

Specific examples of the preparation into which the present compound of the present invention is formulated are shown below.

Preparation Example 1

| Tablet (in 100 mg) | |
| --- | --- |
| The present compound | 1 mg |
| Lactose | 68.4 mg |
| Corn starch | 20 mg |
| Carboxymethylcellulose calcium | 6 mg |
| Hydroxypropyl cellulose | 4 mg |
| Magnesium stearate | 0.6 mg |

Preparation Example 2

| Capsules (in 150 mg) | |
| --- | --- |
| The present compound | 5 mg |
| Lactose | 145 mg |

In the above-mentioned prescriptions, a kind and an amount of the present compound or an additive(s) are optionally changed to prepare a desired preparation.

[Pharmacological Test]

<IL-2 Production Inhibiting Action (1)>

1. Preparation of Compound Solution to be Tested

A suitable amount of Compound 2 to be tested was weighed, dissolved in dimethylsulfoxide (DMSO), and so prepared to be at the final concentration using a culture solution.

2. Test Method (1) Measurement of Transcriptional Activation

Luciferase Assay was carried out according to the conventional method (Aratani et al., Mol. Cell. Biol. 21 (14): pp. 4460-4469 (2001)). That is, Jurkat cells (TIB-152 clone) derived from a human leukemia patient purchased from ATCC were cultured according to the conventional manner and were used for the experiment. Jurkat cells were so seeded to a plate that these became $2.5 \times 10^5$ cells, and 0.5 μg of IL-2 Gene Promoter Reporter Vector purchased from Affymetrix/Panomics, and 5 ng of vector pRL-TK purchased from Promega K.K. were subjected to transfection according to the protocol of Lipofectamine 2000 (Invitrogene) which is a transgenic reagent. That is, 2 μl of Lipofectamine 2000 was used based on 1 μg of a plasmid, and mixed with the Plasmid in Opti-MEM and added to the cells after 20 minutes.

After the reaction for 20 minutes, to Jurkat cells into which IL-2 Gene Promoter Reporter Vector has been transduced was added A23187 (Sigma) or DMSO which is a transcriptional activation agent of IL-2 so that the final concentration became 0.3 μM, and seeded to 24-well plate so that these became $2.5 \times 10^5$ cells. Compound 2 was added thereto so that the final concentration became 0.3 μM, 1 μM or 10 μM, respectively, and cultured in a 37° C. incubator (setting: 37° C., 5% $CO_2$/95% air). After 24 hours, the cells were recovered, dissolved in Passive Lysis Buffer (Promega), and Luciferase activity was measured by using Dual-Luciferase Reporter Assay which is a commercially available Luc activity measurement kit (Promega) and using a luminometer (Centro XS3 LB-960 of Berthold).

3. Calculation Formula of IL-2 Transcriptional Activity

Each experiment was carried out with 3 sample numbers, and corrected by the Dual Lusiferase method. Luc activity value was obtained by dividing the measured value with the value of control (pRL-TK activity), and the value when DMSO had been added was 1. Further, according to the following numerical formula, an inhibition ratio of the IL-2 transcriptional activation was calculated.

Inhibition ratio=(1-Luc activity value when stimulation by A23187 of compound to be tested has been done/Luc activity value when stimulation by A23187 of DMSO has been done)×100(%)

4. Results and Discussion

The results are shown in Table 1. The Luc value shows an average value (number of examples: 3). As a result, transcriptional activation of IL-2 was significantly accelerated by the stimulation of A23187. To this acceleration, Compound 2 showed a statistically significant inhibiting action. From the results as mentioned above, it has been suggested that the present compound in the present invention inhibited IL-2 transcriptional activation, and was useful as an IL-2 production inhibitor or a prophylactic or therapeutic agent of IL-2 related diseases.

TABLE 1

Action of Compound 2 to transcriptional activation of IL-2

| Drug | Concentration | No stimulation | Stimulated by A23187 | Inhibiting ratio |
| --- | --- | --- | --- | --- |
| DMSO | — | 1.0000 ± 0.0590 | 92.6521 ± 6.5985 | — |
| Compound 2 | 0.3 μM | 0.8842 ± 0.1143 | 81.9510 ± 30.4537 | 12% |
| Compound 2 | 1 μM | 0.9410 ± 0.0598 | 65.0761 ± 13.2402 | 30% |
| Compound 2 | 10 μM | 0.9469 ± 0.0928 | 27.5064 ± 29.2861 | 70% |

The value of an average value±a standard deviation is shown.

<IL-2 Production Inhibiting Action (2)>

Preparation of Compound Solution and Assay Method

With regard to Compounds 3, 4 and 5 to be tested and comparative compounds asimadoline and U-50488, compound solutions to be tested were prepared similar to the IL-2 production inhibiting action (1), and IL-2 transcription inhibiting activity was measured.

Results and Discussion

The results are shown in Table 2. Compounds 3, 4 and 5 inhibited transcriptional activation of IL-2, and their inhibition ratios were larger than the inhibition ratios of asimadoline and U-50488 which were also the κ opioid receptor agonist. From the results as mentioned above, it has been suggested that the present compound in the present invention inhibited IL-2 transcriptional activation, and was useful as an IL-2 production inhibitor or a prophylactic or therapeutic agent of IL-2 related diseases.

TABLE 2

Action of each compound to transcriptional activation of IL-2

| Drug | Concentration | Inhibition ratio |
| --- | --- | --- |
| Compound 3 | 10 μM | 77% |
| Compound 4 | 10 μM | 38% |
| Compound 5 | 10 μM | 72% |
| Asimadoline | 10 μM | 19% |
| U-50488 | 10 μM | 15% |

UTILIZABILITY IN INDUSTRY

The present invention is useful as an IL-2 production inhibitor or a prophylactic or therapeutic agent of IL-2 related diseases.

The invention claimed is:

1. A method for treatment of a disease selected from the group consisting of polymyositis, ankylosing spondylitis, systemic sclerosis, Sjogren's syndrome, and scleroderma the method comprising administering an effective amount of a compound represented by the formula (I):

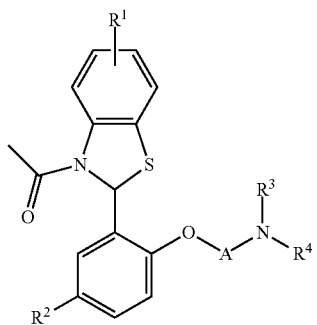

wherein
A represents a lower alkylene group;
$R^1$ represents a hydrogen atom, a halogen atom, a lower alkyl group or a lower alkyl group substituted by a halogen atom;
$R^2$ represents a hydrogen atom, a halogen atom, a lower alkyl group or a lower alkoxy group; and
$R^3$ and $R^4$ each may be the same or different from each other and represent a hydrogen atom, a lower alkyl group, a lower alkyl group substituted by a hydroxyl group, a lower alkyl group substituted by a lower alkoxy group, a lower alkyl group substituted by a lower alkoxy group which is substituted by a lower alkoxy group or a lower alkyl group substituted by an acetoxy group,
or a pharmaceutically acceptable salt thereof as an active ingredient.

2. The method according to claim 1, wherein the compound represented by the formula (I) is a compound wherein
A represents a lower alkylene group;
$R^1$ represents a halogen atom;
$R^2$ represents a lower alkoxy group;
$R^3$ represents a lower alkyl group; and
$R^4$ represents a lower alkyl group substituted by a hydroxyl group, a lower alkyl group substituted by a lower alkoxy group, a lower alkyl group substituted by a lower alkoxy group which is substituted by a lower alkoxy group or a lower alkyl group substituted by an acetoxy group.

3. The method according to claim 1, wherein the compound represented by the formula (I) is a compound where
A represents trimethylene group or 1-methyltrimethylene group;
$R^1$ represents chlorine atom;
$R^2$ represents methoxy group;
$R^3$ represents isopropyl group; and
$R^4$ represents 2-hydroxyethyl group, 2-methoxyethyl group, 2-ethoxyethyl group, 2-(methoxymethoxy)ethyl group or 2-acetoxyethyl group.

4. The method according to claim 1, wherein
the compound represented by the formula (I) is (+)-3-acetyl-6-chloro-2-[2-(3-(N-(2-ethoxyethyl)-N-isopropylamino)propoxy)-5-methoxyphenyl]benzothiazoline, (±)-3-acetyl-6-chloro-2-[2-(3-(N-(2-ethoxyethyl)-N-isopropylamino)propoxy)-5-methoxy-phenyl]benzothiazoline, (+)-3-acetyl-6-chloro-2-[2-(3-(N-(2-hydroxyethyl)-N-isopropylamino)propoxy)-5-methoxyphenyl]benzothiazoline or (+)-3-acetyl-6-chloro-2-[2-(3-(N-isopropyl-N-(2-methoxyethyl)amino)propoxy)-5-methoxyphenyl]benzothiazoline.

5. The method according to claim 1, wherein
the pharmaceutically acceptable salt of the compound represented by the formula (I) is a (−)-O,O'-diacetyl-L-tartaric acid salt or a hydrochloric acid salt.